United States Patent
Morris

(10) Patent No.: US 6,863,439 B2
(45) Date of Patent: Mar. 8, 2005

(54) RADIOGRAPHIC DEVICE HAVING AN ADJUSTABLE HEAD

(75) Inventor: William W. Morris, Woodstock, IL (US)

(73) Assignee: X-cel X-ray Corporation, Crystal Lake, IL (US)

(*) Notice: Subject to any disclaimer, the term of this patent is extended or adjusted under 35 U.S.C. 154(b) by 20 days.

(21) Appl. No.: 10/630,040

(22) Filed: Jul. 30, 2003

(65) Prior Publication Data

US 2005/0025286 A1 Feb. 3, 2005

(51) Int. Cl.⁷ .................................................. A61B 6/04
(52) U.S. Cl. ........................ 378/192; 378/193; 378/196
(58) Field of Search .............................. 378/192, 193, 378/196, 197, 55

(56) References Cited

U.S. PATENT DOCUMENTS

| | | | |
|---|---|---|---|
| 3,838,286 A | * | 9/1974 | Prendergast et al ........... 378/26 |
| 4,082,955 A | * | 4/1978 | Sell .............................. 378/26 |
| 4,166,602 A | | 9/1979 | Nilsen et al. |
| 4,532,645 A | | 7/1985 | Morris |
| 4,587,668 A | | 5/1986 | Morris |
| 5,283,823 A | | 2/1994 | Morris |
| 5,301,659 A | * | 4/1994 | Brisson et al. ................. 601/4 |
| 5,388,142 A | | 2/1995 | Morris |

\* cited by examiner

Primary Examiner—Craig E. Church
Assistant Examiner—Irakli Kiknadze
(74) Attorney, Agent, or Firm—Marshall, Gerstein & Borun LLP

(57) ABSTRACT

A radiographic device includes a platform defining a lateral and longitudinal directions and a mounting assembly having a first end pivotably coupled to the platform and a second end, wherein the second end is movable in the lateral and longitudinal directions. A yoke has a first bracket with a cross support coupled to the mounting assembly second end for pivoting about a Y axis extending parallel to the longitudinal direction, and spaced first and second arms are coupled to the cross support. A radiographic head is pivotably coupled to the first and second arms of the first bracket at points along an X axis extending parallel to the lateral direction, wherein the radiographic head is pivotable about the X axis.

7 Claims, 3 Drawing Sheets

RADIOGRAPHIC DEVICE HAVING AN ADJUSTABLE HEAD

FIELD OF THE INVENTION

The present invention generally relates to radiographic devices and, more particularly, to adjustable supports for radiographic heads used in x-ray equipment.

BACKGROUND OF THE INVENTION

Various types of radiographic devices are generally known in the art. A known x-ray unit for podiatry is disclosed in U.S. Pat. No. 4,587,668, which is assigned to the same assignee as the present disclosure. Generally, such x-ray units include a platform upon which a patient places his or her feet to be x-rayed. The platform is raised above floor level to allow film cassettes to be positioned in a film well located below the platform. The platform may further include a slot for receiving a vertically oriented film cassette. A radiographic head is mounted on vertical mounting members which serve to space the radiographic head a desired distance above the foot platform. The vertical mounting members are moveable in both the lateral and longitudinal directions so that x-rays of a patient's feet can be taken from many angles.

Previous radiographic devices used for podiatry accommodate lateral movement of the vertical mounting members by allowing the radiographic head to pivot about an axis parallel to the longitudinal direction, referred to herein as the Y axis. Such devices typically include a horizontal mounting member that is coupled to a top end of the vertical mounting members and defines a socket. The radiographic head includes a mounting bracket having a stub shaft sized for insertion into the socket, so that the bracket may be rotated with respect to the horizontal mounting member. A set screw is provided for holding the bracket and attached radiographic head in a desired orientation with respect to the horizontal mounting member. When the vertical mounting members are adjusted in a lateral direction, the radiographic head may be rotated about the Y axis so that it is directed toward the appropriate target area on the platform.

While such previous radiographic devices perform satisfactorily in many instances, problems exist in connection with obtaining certain combinations of projections commonly taken during foot x-rays. Podiatrists may require any combination of lateral, medial oblique, anteroposterior ("AP"), or other projections. The lateral and medial oblique projections can be taken without requiring patients to move to their feet. To obtain an AP projection with the foregoing devices, however, requires patients to move their feet 90 degrees from the foot position used for the lateral and medial oblique projections. Repositioning feet for different views is often difficult or dangerous for elderly patients or individuals whose balance or ability to move on the platform is impaired due to disease or other conditions, such as arthritis. Accordingly, a radiographic device is needed in which a combination of AP and other projections may be taken without requiring the patient to change feet position and/or orientation.

Figure 1:
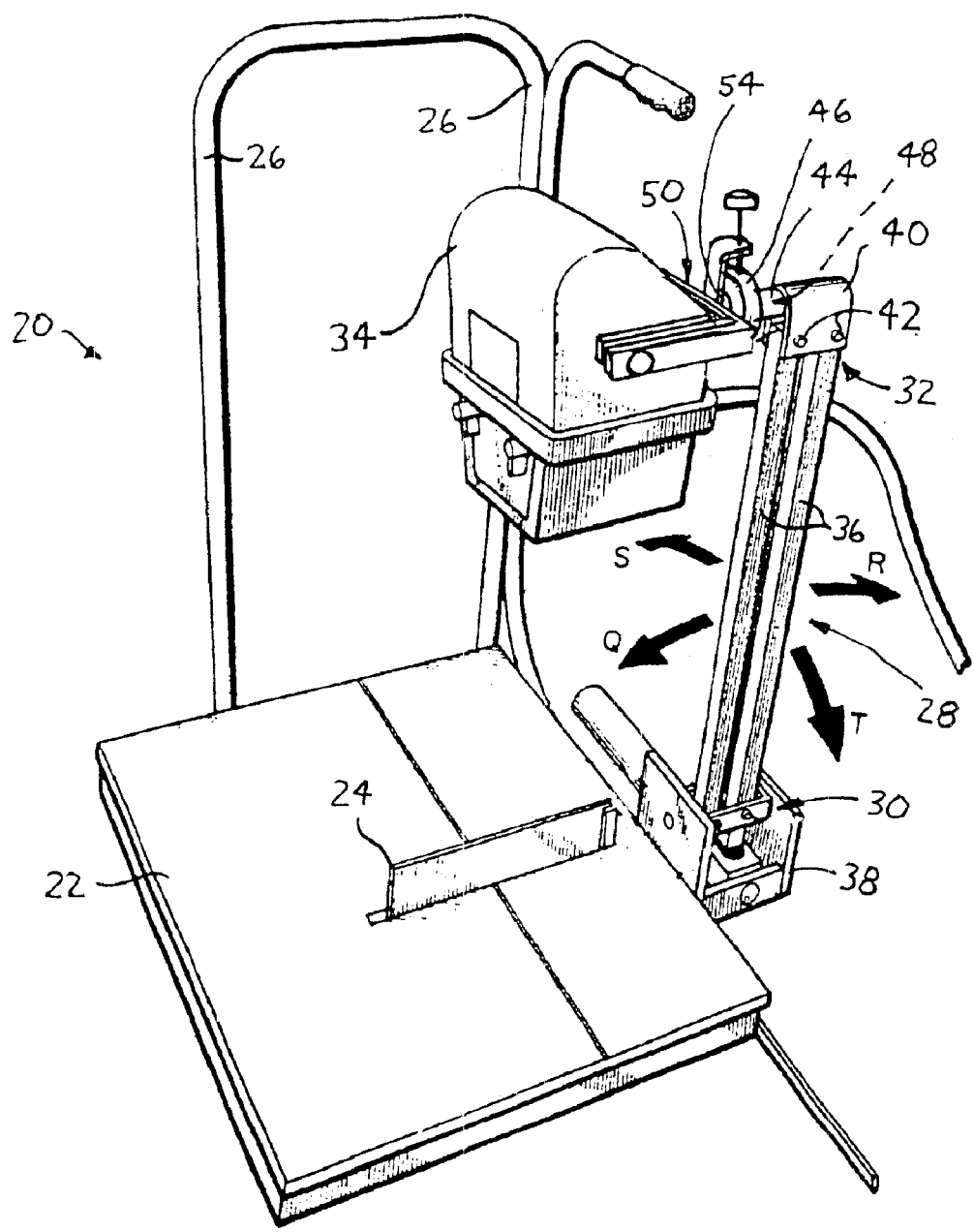
FIG. 1 is a perspective view of a radiographic device constructed in accordance with the teachings of the disclosure.

While the following detailed description sets forth various modifications and alternative constructions, certain illustrative embodiments thereof have been shown in the drawings and will be described below in detail. It should be understood, however, that there is no intention to limit the disclosure to these specific forms disclosed, but on the contrary, the intention is to cover all modifications, alternative constructions, and equivalents falling within the spirit and scope of the invention as defined by the appended claims.

DETAILED DESCRIPTION

Referring now to the drawings, and with specific reference to FIG. 1, the radiographic device constructed in accordance with the teachings of the disclosure is generally referred to by reference numeral 20. The radiographic device 20 is described and illustrated herein for use in podiatry treatment, but the teachings provided herein may be applied to radiographic devices used in other fields.

The radiographic device 20 includes a foot platform 22 and a removable foot separation plate 24 extending perpendicular to the platform 22. A film cartridge may be inserted either in the foot separation plate 24 or a tray positioned below the platform 22, depending upon the desired x-ray view. Hand rail legs 26 are mounted to the platform 22 and provide a patient support hand rail.

As shown in FIG. 1, a head mounting assembly 28 has a first end 30 pivotably coupled to the platform 22 and a second end 32 connected to the radiographic head 34. As used herein, the radiographic head is meant to include a power source and an associated collimator which is attached to and depends from the power source. The power source is capable of emitting electromagnetic radiation sufficient to generate x-ray images. The mounting assembly 28 includes a pair of vertical mounting members 36 having lower ends disposed in a mounting apparatus 38. The mounting apparatus 38 may include spring loaded mounting means for holding the vertical mounting members 36 in a desired position, such as the mounting means disclosed in U.S. Pat. No. 4,587,668, assigned to the current assignee and incorporated herein by reference. Alternatively, other means for holding the vertical mounting members 36 in place may also be used. The upper ends of the vertical mounting members 36 are coupled to a U-shaped mounting plate 40 using bolts 42. A horizontal mounting member 44 has a first end attached to the U-shaped mounting plate 40 and a free second end carrying a collar 46. The horizontal mounting member 44 is hollow to define an internal socket 48.

A yoke 50 is provided for coupling the radiographic head 34 to the mounting assembly 28 and allowing angular adjustment not only about the Y axis, but also about an axis that is parallel to the lateral direction, referred to herein as the X axis. In the illustrated embodiment, the yoke 50 includes an outer bracket 52 having a stub shaft 54 sized for insertion into the socket 48 of the horizontal member 44. The outer bracket 52 includes a cross support 56 attached to the stub shaft 54 and spaced, generally parallel outer arms 58 attached to opposite ends of the cross support 56.

In the illustrated embodiment, the yoke 50 further includes an inner bracket 60 attached to a back plate 62 of the radiographic head 34. The inner bracket 60 includes a cross member 64 spanning a width of the radiographic head and two inner arms 66 attached to opposite ends of the cross member 64. The inner bracket 60 is sized to closely fit inside the outer bracket 52 so that, when the radiographic head 34 is oriented in the position shown in FIG. 3, the outer arms 58 overlie the inner arms 66. The back plate 62 includes a threaded aperture 63 for receiving a fastener 65. The fastener 65 passes through a hole in the cross member 64 thereby to secure the inner bracket 60 to the radiographic head back plate 62. Pins 68 are attached to the inner arms 66 and pass through holes formed in the outer arms 58 to pivotably couple the inner bracket 60 to the outer bracket 52. Free ends of the pins 68 are threaded to receive knobs 70 which may be rotated to secure the inner bracket 60 and radiographic head 34 at a desired angle with respect to the outer bracket 52.

The outer bracket 52 further includes a set screw assembly having a bracket 72 attached to the cross support 56. A threaded aperture 74 is formed in the bracket 72 and is sized to receive a set screw 76. The set screw 76 has a length sufficient so that an end of the set screw is engageable with the collar 46. As a result, the set screw 76 may be loosened to allow the stub shaft 54 of the yoke 50 to rotate within the socket 48, thereby adjusting the angle of the radiographic head 34 about the X axis. The set screw 76 may then be tightened to engage the collar 46 thereby locking the yoke 50 and attached radiographic head 34 in the desired position.

Figure 2:
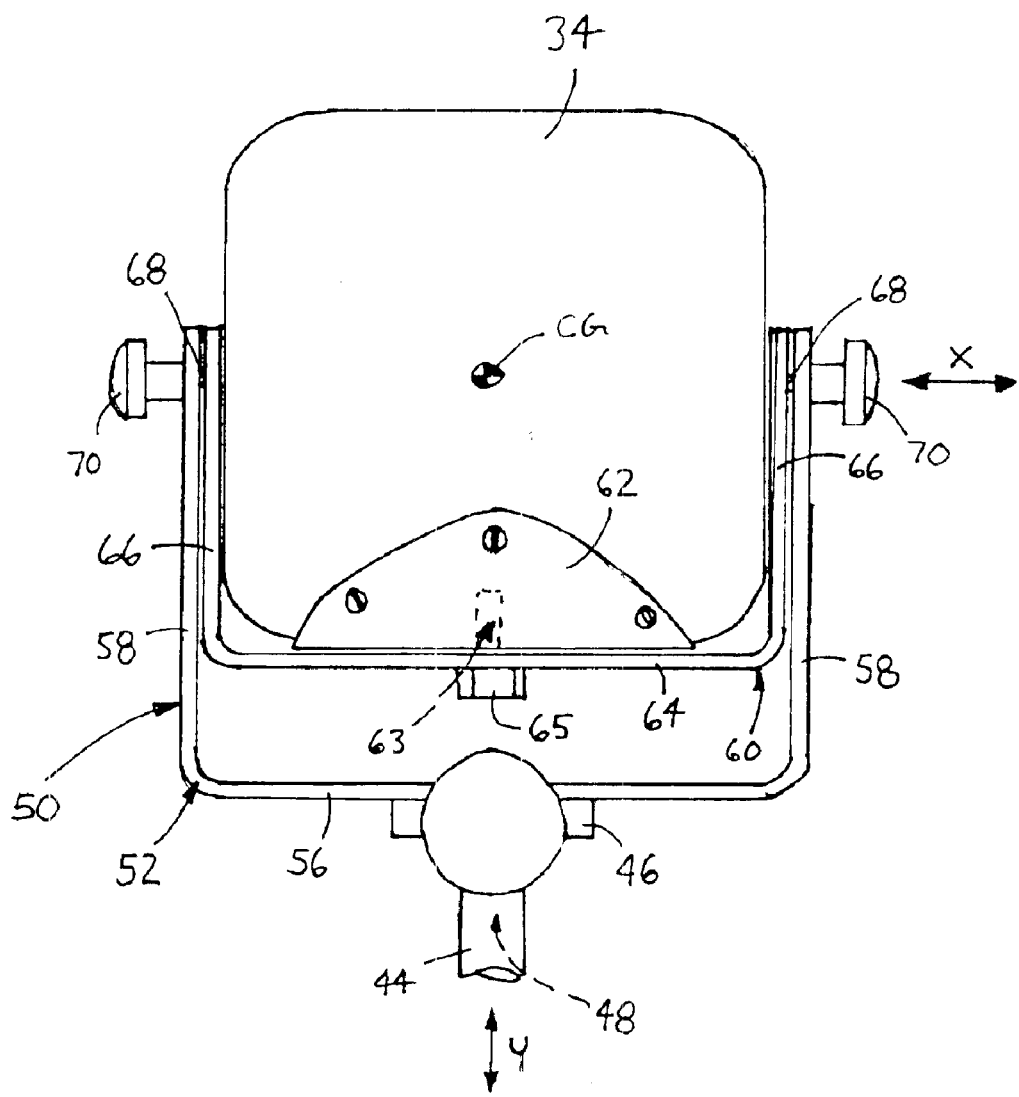
FIG. 2 is a plan view of a radiographic head incorporated in the radiographic device of FIG. 1.

It may be desirable to locate the pins 68 and the stub shaft 54 with respect to the radiographic head center of gravity (CG) so that the desired lateral and longitudinal tilt of the radiographic head 34 is held prior to tightening of the knobs 70. In the illustrated embodiment, the pins 68 are located along a lateral axis passing through the center of gravity (CG) of the radiographic head 34, identified in FIG. 2 as doubled-ended arrow X. These points which lay on the lateral X axis are referred to herein as "balance points." In addition, the stub shaft 54 is located at a center of the cross support 56 so that the stub shaft 54 is located along a longitudinal axis passing through the radiographic head center of gravity (CG), identified in FIG. 2 as double-ended arrow Y. As a result, the outer bracket 52 is attached to the inner bracket 60 such that the radiographic head 34 will remain substantially in the desired lateral angle prior to tightening of the knobs 70.

Figure 3:
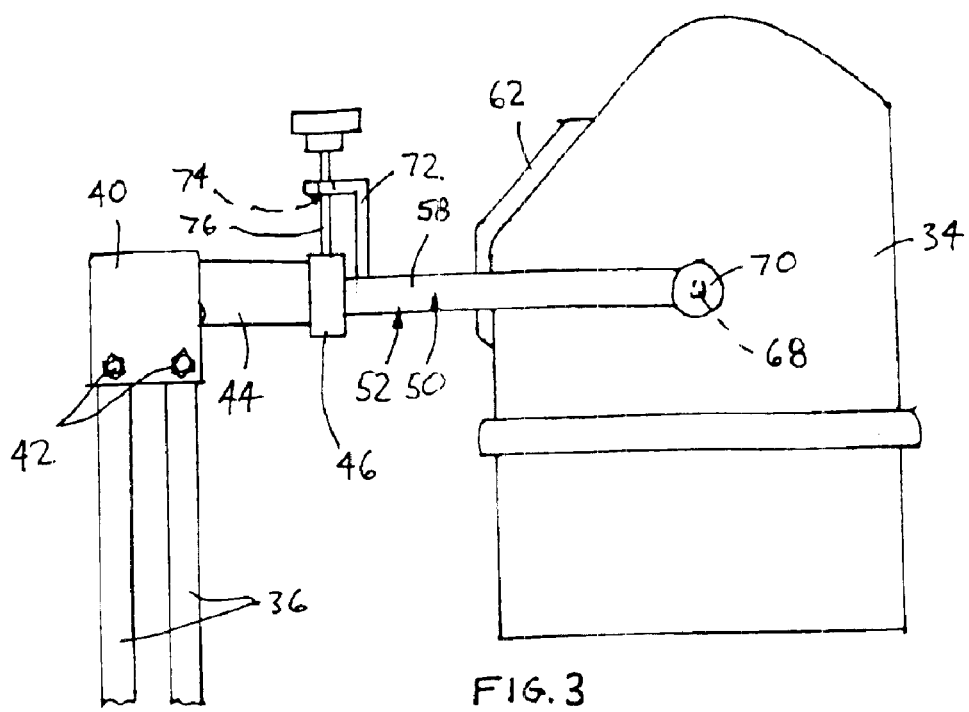
FIG. 3 is a side view of a radiographic head oriented to take a substantially vertical projection.
Figure 4:
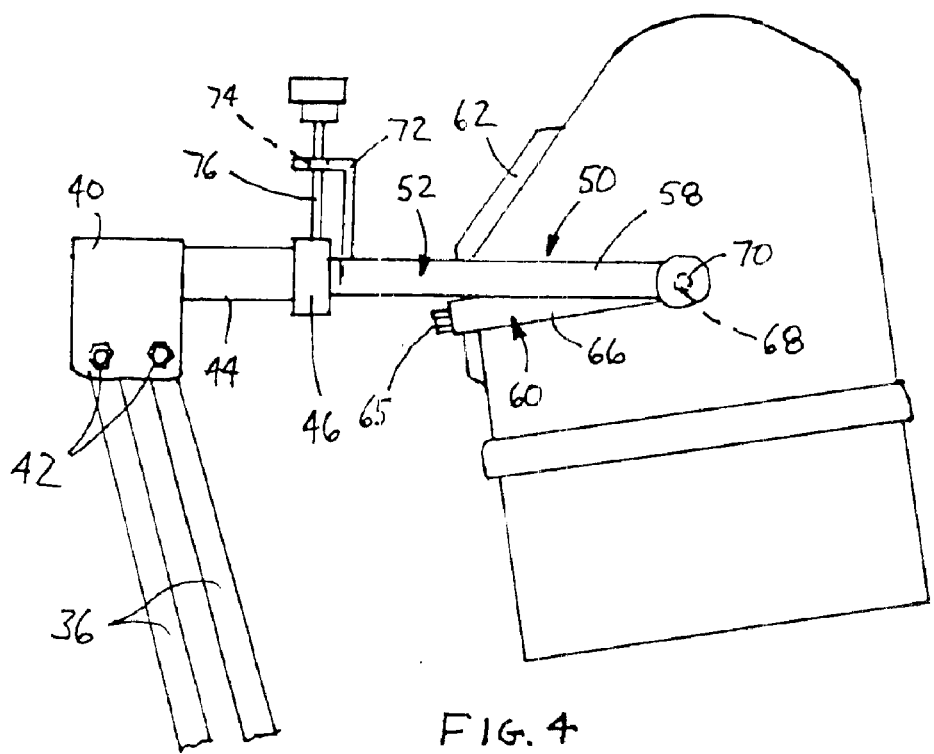
FIG. 4 is a side view of the radiographic head tilted to obtain an angled projection.

The radiographic device 20 described herein allows the radiographic head to be positioned for multiple projections without requiring significant repositioning of the patients feet. For example, the vertical mounting members 36 may be rotated laterally in directions S or T as shown in FIG. 1 and the radiographic head 34 may be rotated about the Y axis defined by the horizontal mounting member 44 and stub shaft 54 to obtain lateral or medial oblique projections. For these projections, the vertical mounting members 36 form substantially a right angle to the longitudinal direction, as illustrated at FIG. 3. In addition, the vertical mounting members 36 may be rotated longitudinally in directions Q and R and the outer bracket 52 of the yoke 50 may be adjusted to an appropriate angle about the X axis defined by the pins 68 to obtain additional projections such as the AP projection, as illustrated at FIG. 4. The yoke 50 allows the radiographic head 34 to be tilted about the X axis so that the radiographic head 34 is directed to substantially the same target area. As a result, the different projections, and any combination thereof, are obtained with the patient's feet remaining in substantially the same position.

The illustrated embodiment is particularly suited for retrofit installation where the radiographic device includes a radiographic head having a back plate. The back plate of such devices typically has the stub shaft and set screw assembly directly attached thereto. Accordingly, to retrofit the current yoke 50 onto an existing radiographic device, the existing stub shaft and set screw assembly are removed either individually or with the existing back plate as a unit. If removed individually, the yoke 50 is attached simply by forming threaded apertures 63 in the back plate (if not present already) and securing the inner bracket 60 to the existing back plate with the fastener 65. Otherwise, a new back plate 62 is attached to the radiographic head 34 having the threaded aperture 63 formed therein, and the inner bracket 60 is secured to the new back plate 62 using the fastener 65. In either alternative, the stub shaft 54 of the yoke 50 is inserted into the socket 48 defined by the horizontal mounting member 44.

In addition to retrofit applications, the teachings of the present disclosure may be applied to new products. For entirely new radiographic devices, the pins 68 may be supported directly by the housing of the radiographic head 34, thereby obviating the need for the inner bracket 60 and back plate 62. Accordingly, the balance points are located directly on the housing of the radiographic head 34, rather than on the inner bracket 60. In this alternative, the knobs 70 may be tightened to secure the radiographic head 34 in the desired orientation with respect to the outer bracket 52.

The foregoing detailed description has been given for clearness of understanding only, and no unnecessary limitations should be understood therefrom, as modifications would be obvious to those skilled in the art.

I claim:

1. A radiographic device comprising:
   a platform defining a lateral direction and a longitudinal direction;
   a mounting assembly having a first end pivotably coupled to the platform and a second end, wherein the second end is movable in the lateral and longitudinal directions;
   a yoke including a first bracket having a cross support coupled to the mounting assembly second end for pivoting about a Y axis extending parallel to the longitudinal direction a stub shaft attached to a midpoint of the first bracket cross support for coupling to the mounting assembly second end, and spaced first and second arms coupled to the cross support; and
   a radiographic head comprising an X-ray source and defining a center of gravity and being pivotably coupled to the first and second arms of the first bracket at points along an X axis extending parallel to the lateral direction and passing substantially through the radiographic head center of gravity, wherein the radiographic head is pivotable about the X axis wherein the Y axis passes substantially through the radiographic head center of gravity and extends substantially perpendicular to the X axis.

2. The radiographic device of claim 1 in which the radiographic head includes a second bracket removably attached thereto having first and second inner arms extending at least partially across opposite lateral sides of the radiographic head, wherein the first and second inner arms are pivotably coupled to the first and second arms of the first bracket.

3. The radiographic device of claim 2, in which the radiographic head includes a back plate, and in which the second bracket is attached to the back plate with a fastener.

4. The radiographic device of claim 1, in which the radiographic head is pivotably connected to the first bracket with first and second pins.

5. The radiographic device of claim 1, in which the first and second pins are threaded to receive tightening knobs.

6. A radiographic device for use in podiatry comprising:
a foot platform defining a lateral direction and a longitudinal direction;
a mounting assembly including first and second vertical mounting members having lower ends pivotably coupled to a mounting apparatus and upper ends attached to a U-shaped mounting plate, and a hollow horizontal mounting member attached to the U-shaped mounting plate, wherein the horizontal mounting member is movable in the lateral and longitudinal directions;
a yoke including an outer bracket having a stub shaft sized for insertion into the horizontal mounting member and rotatable within the horizontal mounting member about a Y axis extending substantially parallel to the longitudinal direction, a cross support attached to the stub shaft, and spaced first and second outer arms attached to the cross support;
a radiographic head comprising an X-ray source and including a back plate and an inner bracket having a cross member attached to the back plate and first and second inner arms extending at least partially across opposite lateral sides of the radiographic head; and
first and second pins rotatably coupling the first and second inner arms to the first and second outer arms, respectively, at points along an X axis extending parallel to the lateral direction, wherein the radiographic head is pivotable about the X axis.

7. The radiographic device of claim 5, in which the radiographic head defines a center of gravity, and in which both the X and Y axes pass substantially through the radiographic head center of gravity.

* * * * *

UNITED STATES PATENT AND TRADEMARK OFFICE
CERTIFICATE OF CORRECTION

PATENT NO. : 6,863,439 B2
DATED : March 8, 2005
INVENTOR(S) : William W. Morris

It is certified that error appears in the above-identified patent and that said Letters Patent is hereby corrected as shown below:

Column 4,
Line 41, please delete "direction" and insert -- direction, --.

Column 6,
Lines 10-11, please delete "parallel" and insert -- substantially parallel --.

Signed and Sealed this

Twelfth Day of July, 2005

JON W. DUDAS
*Director of the United States Patent and Trademark Office*